US011039825B2

(12) United States Patent
Tordi et al.

(10) Patent No.: US 11,039,825 B2
(45) Date of Patent: Jun. 22, 2021

(54) PLATE HOLES SUTURE CONNECTION

(71) Applicant: DePuy Synthes Products, Inc., Raynham, MA (US)

(72) Inventors: Gianluca Tordi, Riccione (IT); Daniel Andermatt, Solothurn (CH); This Aebi, Grenchen (CH)

(73) Assignee: DePuy Synthes Products, Inc., Raynham, MA (US)

( * ) Notice: Subject to any disclaimer, the term of this patent is extended or adjusted under 35 U.S.C. 154(b) by 378 days.

(21) Appl. No.: 15/787,356

(22) Filed: Oct. 18, 2017

(65) Prior Publication Data

US 2018/0110507 A1    Apr. 26, 2018

Related U.S. Application Data

(60) Provisional application No. 62/412,683, filed on Oct. 25, 2016.

(51) Int. Cl.
*A61B 17/04* (2006.01)
*A61B 17/80* (2006.01)
*A61B 17/82* (2006.01)
*A61B 17/88* (2006.01)

(52) U.S. Cl.
CPC .......... *A61B 17/0401* (2013.01); *A61B 17/80* (2013.01); *A61B 17/82* (2013.01); *A61B 17/8883* (2013.01); *A61B 17/8057* (2013.01); *A61B 2017/044* (2013.01); *A61B 2017/0409* (2013.01); *A61B 2017/0414* (2013.01); *A61B 2017/0456* (2013.01)

(58) Field of Classification Search
CPC ............ A61B 17/0401; A61B 17/0642; A61B 2017/0404; A61B 2017/0409; A61B 2017/0411; A61B 2017/049
See application file for complete search history.

(56) References Cited

U.S. PATENT DOCUMENTS

| 6,149,653 A * | 11/2000 | Deslauriers | ........ A61B 17/0401 606/232 |
| 8,343,155 B2 * | 1/2013 | Fisher | ........ A61B 17/80 606/74 |
| 10,499,968 B2 * | 12/2019 | Wiederkehr | ........ A61B 17/82 |

(Continued)

FOREIGN PATENT DOCUMENTS

| CN | 103025257 A | 4/2013 |
| CN | 104080416 A | 10/2014 |

(Continued)

*Primary Examiner* — Anu Ramana
(74) *Attorney, Agent, or Firm* — Fay Kaplun & Marcin, LLP (57) ABSTRACT

A suture connection system and method includes a suture connector having a body configured to be inserted into a hole in a bone plate, the body being threaded to secure the suture connector in to the bone plate. At least one recess extends inwardly from a sidewall of the suture connector to define a proximal engagement portion and a through hole configured to receive a suture extends through the proximal engagement portion and is open to the recess. A driver includes an elongate rod and an engagement element coupled to the distal end of the rod, the engagement element having at least one prong configured to engage the proximal engagement portion to insert the suture connector into the bone plate hole.

17 Claims, 5 Drawing Sheets

(56) References Cited

U.S. PATENT DOCUMENTS

| | | |
|---|---|---|
| 2002/0052629 A1 | 5/2002 | Morgan et al. |
| 2009/0062854 A1 | 3/2009 | Kaiser et al. |
| 2012/0158051 A1 | 6/2012 | Foerster |
| 2013/0123841 A1* | 5/2013 | Lyon .................. A61B 17/0401 606/232 |
| 2014/0052176 A1 | 2/2014 | Conley et al. |

FOREIGN PATENT DOCUMENTS

| | | |
|---|---|---|
| EP | 0916311 | 5/1999 |
| WO | 2010/062379 A1 | 6/2010 |
| WO | 2011/040917 | 4/2011 |

\* cited by examiner

PLATE HOLES SUTURE CONNECTION

PRIORITY CLAIM

The present application claims priority to U.S. Provisional Patent Application Ser. No. 62/412,683 filed on Oct. 25, 2016. The entire disclosure of the above application is expressly incorporated herein by reference.

BACKGROUND

Large bone defects are often treated with implants to assist with healing. Bone plates are often utilized to stabilize damaged or weakened portions of bone, for example, at fracture sites. The bone plates may be placed in the target area using any of a variety of methods. For example, bone plates may generally include openings through which bone fixation elements (such as screws and/or pins) are inserted into the bone to anchor the plates to target portions of bone. In some situations, however, bone fragments require additional stabilization. In such cases, it may be beneficial to use sutures in addition to bone plates and fixation elements to stabilize the fragments and preserve a previously achieved reduction of a fracture. Sutures are often secured to a bone plate by threading the sutures through holes in the plates before the plate is secured to the bone. However, attaching sutures to a bone plate in this manner often limits the suture attachment locations available to a surgeon, particularly after a plate has been attached to the bone.

SUMMARY OF THE INVENTION

The present invention relates to a suture connecting device and method for stabilizing bone fragments using sutures in addition to a bone plate and fixation screws.

In one aspect, a suture connection system is provided. The system includes a suture connector comprising a body configured to be inserted into a hole in a bone plate. The body has a proximal end, a distal end, a length extending between the proximal end and the distal end substantially corresponding to a thickness of the bone plate, and a sidewall. The connector body is threaded to secure the suture connector to the bone plate. The suture connector also includes at least one recess extending inwardly from the sidewall to define a proximal engagement portion. The suture connector further includes a through hole, configured to receive a suture, extending through the proximal engagement portion and open to the recess. The system also includes a driver. The driver includes an elongated rod extending from a proximal end to a distal end along a longitudinal axis of the driver. The driver also includes an engagement element coupled to the distal end of the rod, the engagement element having at least one prong configured to engage the proximal engagement portion. In one embodiment, the engagement element includes two prongs. In another embodiment, the prong includes a cutout. In a further embodiment, the cutout extends from a distal prong face to a rounded proximal cutout edge, the proximal cutout edge aligning with a proximal edge of the through hole so that no portion of the prong obstructs the hole. In a further embodiment, the proximal engagement portion includes two recesses. In another embodiment, the prongs engage lateral faces of the proximal engagement portion. In a further embodiment, the suture connector is sized and shaped to sit flush within the bone plate hole such that no portion of the suture connector extends past an upper surface or a lower surface of the bone plate.

In another aspect, a bone plate assembly is provided. The assembly includes a plate having an upper surface, a lower surface and a plurality of holes extending through the plate from the upper surface to the lower surface. The assembly also includes at least one suture connector positioned in one of the holes of the plate. The suture connector includes a body having a proximal end, a distal end, a sidewall, a first recess defined by the sidewall, and a through hole open to the recess. The first recess defines a proximal engagement portion. The body also includes a threading to threadedly engage the hole of the plate. The assembly also includes a driver extending from a proximal end to a distal end including an engagement element. The engagement element has at least one prong configured to engage the proximal engagement portion. In some embodiments the engagement element includes two prongs. In an embodiment, the prong includes a cutout. In another embodiment, the cutout extends from a distal prong face to a rounded proximal cutout edge, the proximal cutout edge aligning with a proximal edge of the through hole so that no portion of the prong obstructs the through hole. In a further embodiment, the plurality of holes is one of locking or variable angle locking holes. In a further embodiment, the proximal engagement portion includes two recesses. In another embodiment, the prongs engage lateral faces of the proximal engagement portion. In a further embodiment, the suture connector is sized and shaped to sit flush within the bone plate hole such that no portion of the suture connector extends past an upper surface or a lower surface of the bone plate.

In a further aspect, a method of connecting a suture to a bone is provided. The method includes securing a bone plate to the bone, the bone plate having a plurality of holes extending through the plate from an upper surface to a lower surface. The method also includes inserting at least one suture into a suture connector. The suture connector includes a body having a proximal end, a distal end, a side wall, a first recess defined by the sidewall, and a through hole open to the recess, wherein the first recess defines a proximal engagement portion. The body includes a threading to threadedly engage the hole of the plate. The method also includes positioning at least one suture connector at one of the plurality of holes. The method also includes using a driver, rotating the suture connector until the suture connector is threadedly inserted into the hole. The driver includes an elongated rod and an engagement element coupled to the distal end of the rod, the engagement element including at least one prong configured to engage the proximal engagement portion. In an embodiment, rotation of the driver causes the transmission of torsional loads from the driver to the suture connector to rotate the suture connector. In another embodiment, the method for the includes removing the suture connector from the hole, repositioning the suture connector at a second one of the plurality of holes, and inserting the suture connector, using the driver, into the second one of the plurality of holes. In a further embodiment, the engagement element includes two prongs, the prongs configured to engage lateral faces of the proximal engagement portion. In another embodiment, the prong includes a cutout, the cutout extending from a distal prong face to a rounded proximal cutout edge, the proximal cutout edge aligning with a proximal edge of the through hole so that no portion of the prong obstructs the through hole.

DETAILED DESCRIPTION

The present invention may be further understood with reference to the following description and the appended drawings, wherein like elements are referred to with the same reference numerals. The present invention relates to a system and method for treating fractures. In particular, exemplary embodiments of the present invention describe a suture connector and a driver to be used in combination with a bone plate to facilitate reduction of a fracture. An exemplary suture connector comprises a proximal through-hole and a rounded distal portion sized and shaped to threadedly engage a locking or variable-angle locking screw hole so that a user may place the suture connector any of a plurality of locations on the bone plate (i.e., at any location where there is a vacant locking hole or variable angle locking hole). To facilitate insertion and removal from the bone plate, a driver for the suture connector includes a distal engagement feature adapted to positively engage the suture connection device so that the suture connector may be inserted into a selected hole in a bone plate and rotated into the bone plate hole to engage a threading on an external surface of a distal portion of the suture connector with an engaging structure of the bone plate hole. It will be understood by those of skill in the art that the terms proximal and distal, as used herein, are used to refer to a direction toward (proximal) and away from (distal) a user (e.g., surgeon) of the device.

Figure 1:
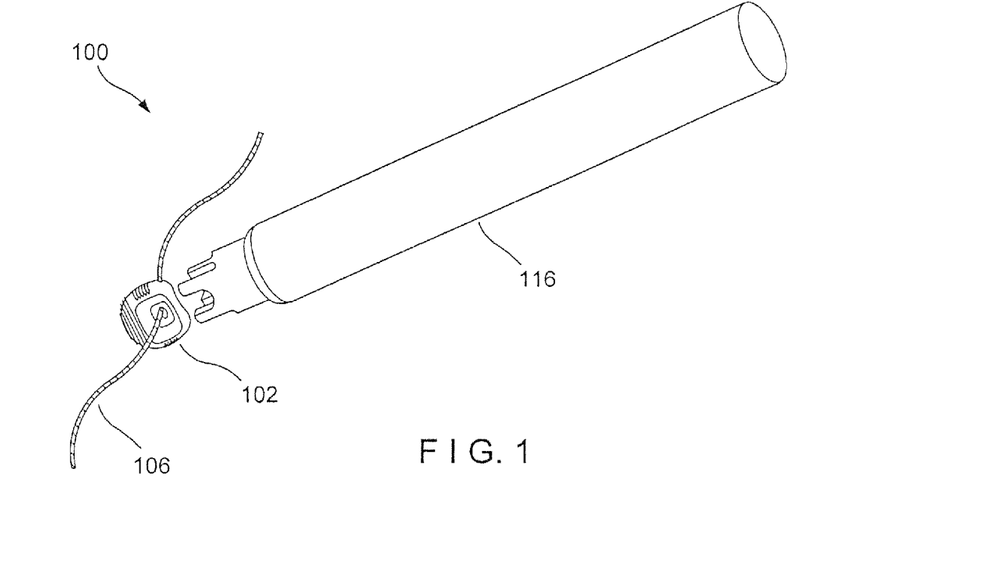
FIG. 1 illustrates a perspective view of an exemplary embodiment of the suture connection system according to the invention.
Figure 2:
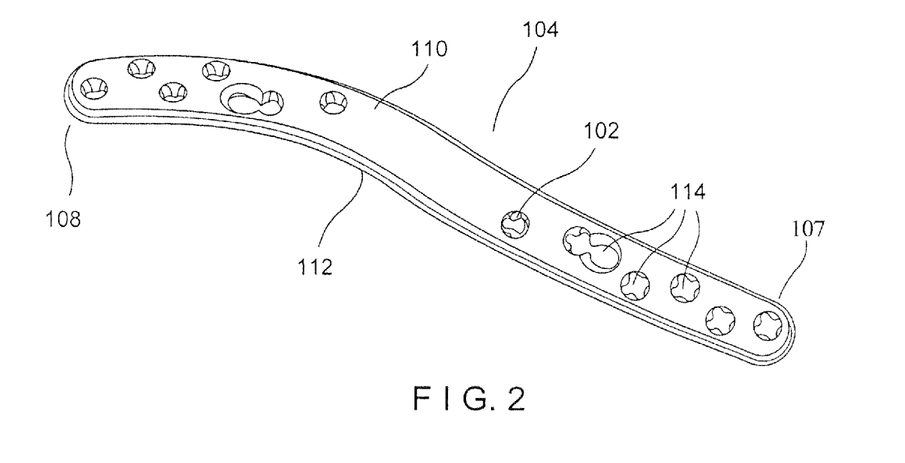
FIG. 2 illustrates a perspective view of the suture connector and bone plate according to an exemplary embodiment of the invention.

As shown in FIG. 1-2, a system 100 according to a first exemplary embodiment of the present invention comprises a driver 116 and a suture connector 102 configured to be coupled to a bone plate 104 to provide a structure for connecting a suture 106 to the bone plate 104 to facilitate reduction of a fracture. In some situations (e.g. involving comminuted fractures), bone fragments may be difficult to stabilize which may make it difficult to sufficiently reduce the fracture and/or to maintain a reduction once it has been achieved. The suture connector 102 facilitates additional stabilization of bone fragments by allowing the suture 106 to be coupled to the plate 104 so that the suture 106 may be wrapped about the bone fragments to prevent movement of the fragments relative to one another. It will be understood by those of skill in the art that the system 100 may include any number of suture connectors 102 and any number of locations at which they may be coupled to the bone plate. Those skilled in the art will understand that the suture connectors 102 permit the connection of a suture 106 to the plate 104 even after the plate 104 has been fixed to one more bone fragments without removing the plate 104 from the bone fragments. That is, because, when connected to the plate 104, the suture-receiving through hole 130 extends away from the outwardly facing first surface 110 of the plate 104 so that the through hole 130 remains accessible to the user even after the plate 104 has been coupled to a portion of bone.

The bone plate 104 extends longitudinally from a first end 107 to a second end 108 and includes a first surface 110 which, when in an operative position, faces away from the bone, and a second surface 112 which, when in an operative position, faces toward the bone. The bone plate 104 further includes a plurality of holes 114 extending therethrough, from the first surface 110 to the second surface 112. The holes 114 may be configured as locking and variable angle locking holes each being adapted to receive either a suture connector 102 or a locking head of a bone fixation element such as a locking screw with a threaded head. Of course, the plate 104 may also include any number of additional holes not configured as locking or variable angle locking holes such as non-locking holes, combination holes, etc. Those skilled in the art will understand that the suture connectors 102 may be coupled to any hole or any part of a hole configured to lockingly engage a head of a bone screw but that other holes may be included in the plate 104 as desired. The holes 114 include an engagement mechanism, such as, for example, a threading (not shown) along an inner surface thereof for engaging a head of a bone fixation element or a suture connector 102. It will be understood by those of skill in the art that the bone plate 104 may be any kind of bone plate that may be used to fix fractures. The bone plate 104 shown in FIG. 2 is an example of the bone plate 104, however, it will be appreciated by one skilled in the art that the bone plate 104 may be provided in varying forms while being in accordance with the present invention herein. For example, the bone plate may be substantially rectangular, circular, or any other shape and may be configured for application on any desired bone or any desired portion of any bone. The bone plate 104 may be provided with holes 114 disposed in a single line, parallel lines, offset from one another, or staggered about the bone plate 104 or in any other desired pattern. The example shown includes standard locking holes configured to lockingly engage the heads of standard bone fixation elements such as screw and pins. However, those skilled in the art will understand that this is merely exemplary and a plate of any desired configuration may be used so long as it includes at least one hole configured to lockingly engage a suture connector 102 or a bone fixation element.

Figure 3A:
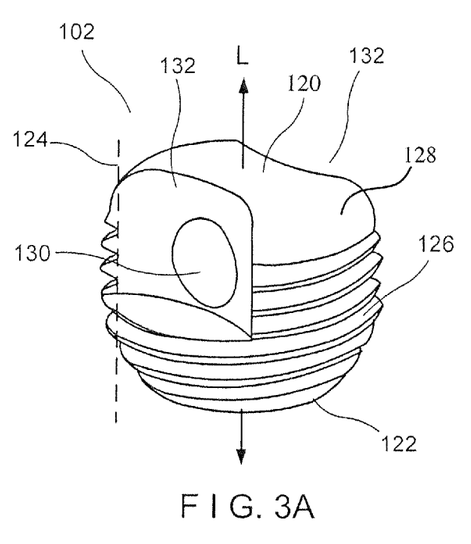
FIG. 3A illustrates a perspective side view of the suture connector according to the embodiment of FIG. 1.
Figure 3B:
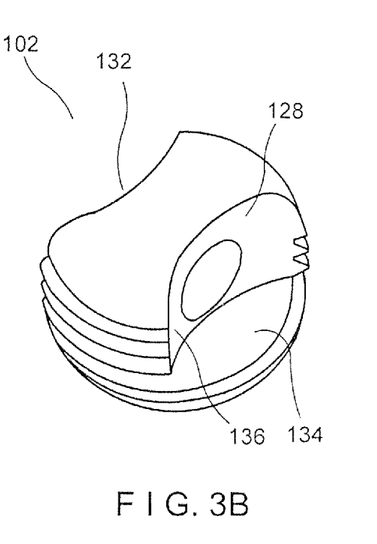
FIG. 3B illustrates perspective top view of the suture connector according to the exemplary embodiment of FIG. 1.

As shown in FIGS. 3A-3B, the suture connector 102 has a body 118 configured to be threadedly inserted into one of the holes 114 of the bone plate 104. In an example, the body 118 of the suture connector 102 is dimensioned and shaped substantially similarly to a threaded head of a conventional locking screw. For example, the body 118 of this embodiment is substantially rounded and has a proximal end 120, a distal end 122, a length extending between the proximal end 120 and the distal end 122 less than or equal to a thickness of the plate 104, and a rounded sidewall 124 (denoted by the dashed line in FIG. 3A) extending between the proximal end 120 and the distal end 122. An outer surface of the connector 102 is provided with at least one plate engaging structure, e.g., threading 126. The threading 126 is preferably dimensioned to engage threading in the plate hole within which it is to be mounted—e.g., a conventional bone plate locking hole or variable angle locking hole. In an exemplary embodiment, the suture connector 102 has dimensions corresponding to the dimensions of a conventional locking screw head so as to easily engage and fit within the holes 114 of the bone plate 104. A proximal portion 128 of the body 118 is configured as an engagement portion. The proximal portion 128 includes a through hole 130 for insertion of a suture 106. The through hole 130 may be any size suitable for easy passage of a suture 106 and may take any shape as desired, for example, the minimize a profile of the plate 104 when combined with one or more suture connectors 102. For example, the through hole 130 may have a diameter equal to or slightly larger than the diameter of the suture 106 to be used or the through hole 130 may be asymmetric with an extent in a direction parallel to an axis of the body 118 being only slightly larger than a thickness of the suture to be inserted therethrough while a dimension of the through hole 130 perpendicular to this axis may be made larger to facilitate insertion of the suture therein without increasing a profile of the plate 104/suture connector 102 combination. The through hole 130 is open to two recesses 132. Recesses 132 extend from the sidewall inwardly toward the longitudinal axis of the body 118 and from a mid-portion of the body 118 to the proximal end 120 of the body 118. Each recess 132 includes a proximally-facing distal face 134 extending transverse to the longitudinal axis of the suture connector 102 and an outwardly-facing side face 136. Side face 136 may be substantially flat or may be concavely curved. Through hole 130 is in communication with recesses 132, extending through the proximal portion 128 of the body 118 from a first recess to the second recess. The proximal portion of the suture connector 102, including recesses 132 and the proximal body portion 128 is sized and shaped to engage a portion of driving tool 116 used to rotate the suture connector 102 into threaded engagement with hole 114 as would be understood by those skilled in the art to releasably fix the suture connector 102 to the bone plate 104. For example, the recesses 132 are sized and shaped to receive a correspondingly shaped portion of the driving tool 116. Suture connector 102 may be formed of any suitable material such as, for example, any biocompatible material of suitable strength such as stainless steel or titanium.

Figure 4:
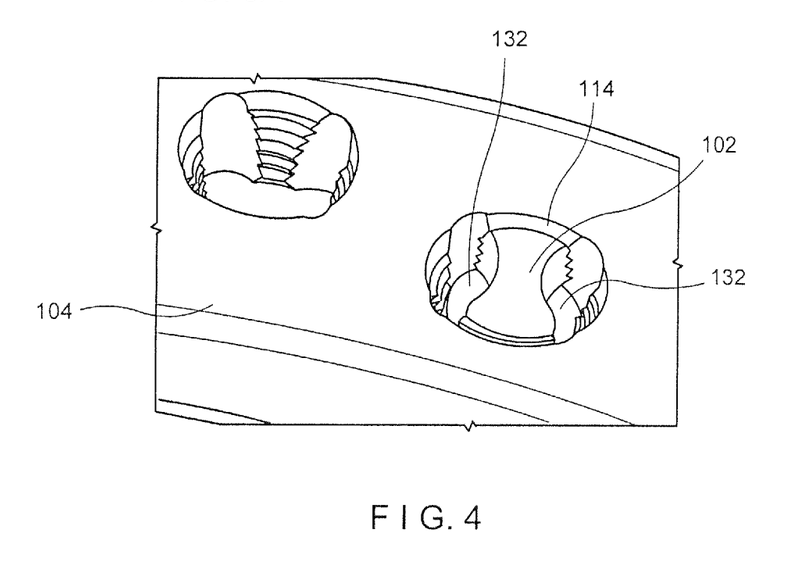
FIG. 4 illustrates a perspective view of the suture connector inserted into the bone plate.
Figure 5:
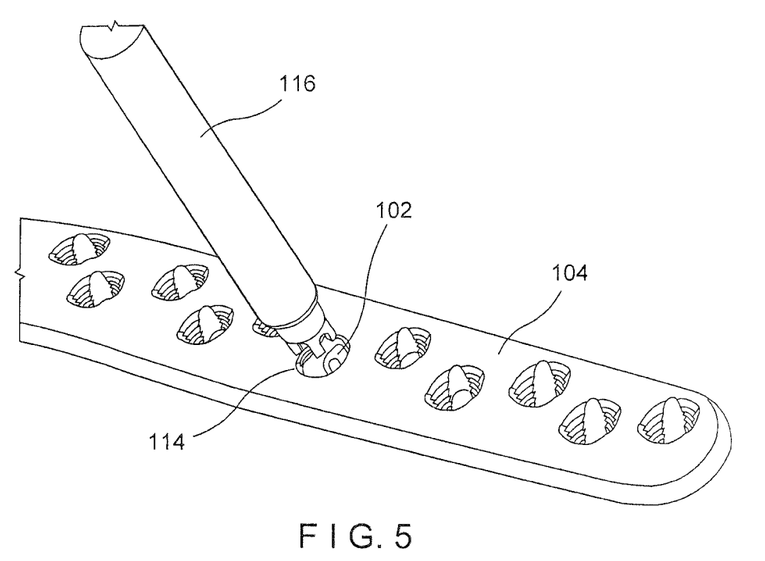
FIG. 5 illustrates a perspective view of the system according to the embodiment of FIG. 1.

As shown in FIGS. 4-5, when inserted into the hole 114, the suture connector 102 sits flush in the plate hole such that neither the proximal end 120 nor the distal end 122 extends past the first or second surfaces of the plate 104. Thus, irritation of surrounding tissue is minimized. As can be seen in the figures, the recesses 132 provide a space between the inner wall of the hole 114 and the exterior of the body 118 of the suture connector 102 so that an engagement portion 136 of a corresponding driving tool 116 may be easily inserted into the hole 114, facilitating easy insertion of the connector 102 into the plate 104 and removal of the suture connector 102 from the plate 104. Furthermore, sutures 106 may also be easily inserted into or removed from the through hole 130 as would be understood by those skilled in the art.

Figure 6:
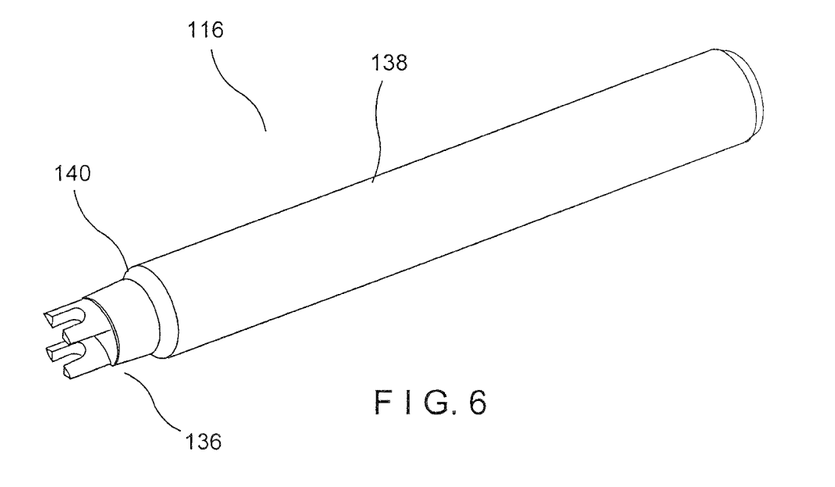
FIG. 6 illustrates a perspective side view of the driver according to the exemplary embodiment of FIG. 1.
Figure 7:
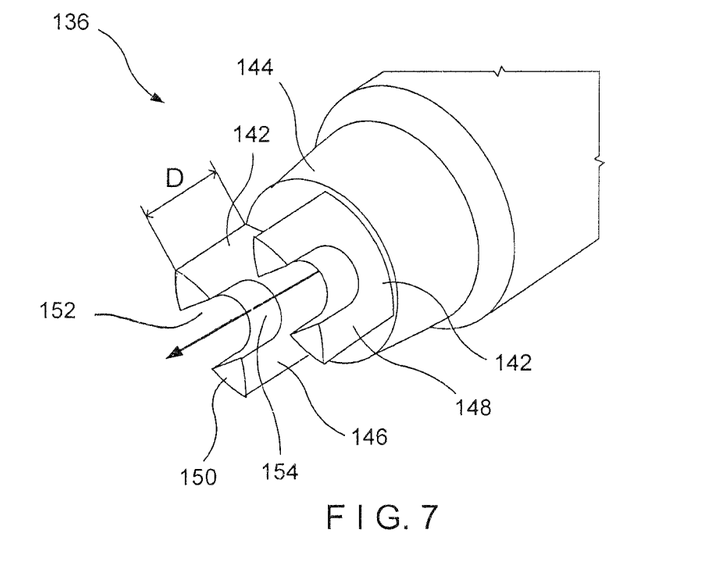
FIG. 7 illustrates a perspective view of the engagement portion of the driver according to the exemplary embodiment.
Figure 8:
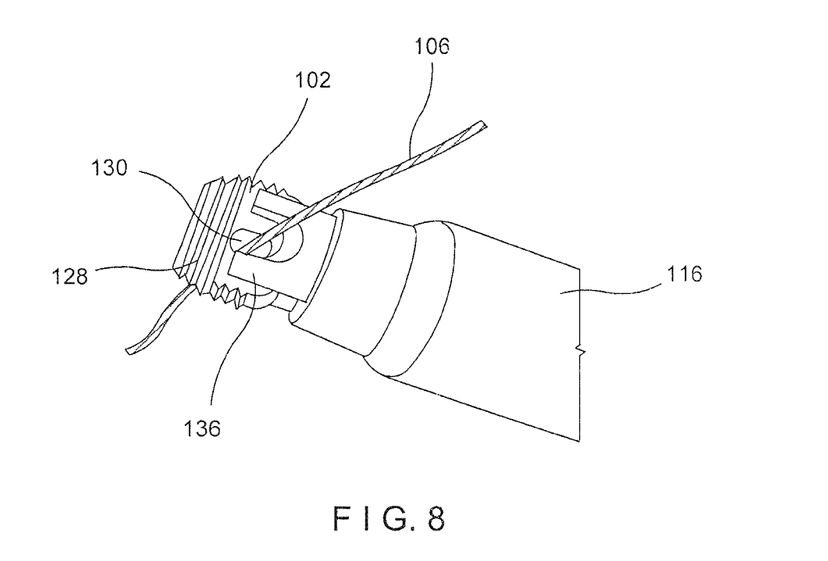
FIG. 8 illustrates a perspective view of the driver, suture connector and suture according to the exemplary embodiment.

Referring to FIGS. 6-7, the driver 116 comprises a rod 138 extending along a longitudinal axis and an engagement portion 136 coupled to a distal end 140 of the rod 138. In an exemplary embodiment, the rod 138 is substantially cylindrical. However, as those skilled in the art will understand the shape of the outer surface of the rod 138 may be any desired shape without departing from the scope of the invention. The outer surface of the driver 116, including the rod 138 and the engagement portion 136, may be made smooth and uninterrupted to minimize abrasion or irritation of surrounding tissue as the driver 116 is rotated about its axis to drive a suture connector 102 into or out of the bone plate 104. The engagement portion 136 may have a diameter that is less that the diameter of the rod 138. Engagement portion 136 includes two prongs 142 extending distally from a base portion 144. The prongs 142 are laterally offset from the longitudinal axis of the driver 116 a distance, D, corresponding to the width of the proximal engagement portion 128 of the suture connector body 118. In an exemplary embodiment, D is equal to or slightly larger than a width of the proximal portion 128 so that the prongs 142 may be easily slid into engagement on either side of proximal portion 128. Prongs 142 may be substantially oval in shape and each has an inner surface 146, an outer surface 148 and a distal face 150. Distal face 150 may be substantially flat or may be rounded. Each prong 142 includes an elongated cutout 152 extending proximally from the distal face to a proximal curved edge 154. Cutouts 152 extend the width of the prongs 142 from the inner surface 146 to the outer surface 148. A curved proximal edge 154 corresponds to the curve of the through hole 130. Specifically, the cutout 152 is configured so that the proximal edge 154 aligns with, or is slightly more proximal than a proximal edge of the through hole 130 so that the no portion of the through hole 130 is obstructed when the driver 116 is in engaged with the suture connector 102, as can be seen in FIG. 8. When in the engaged position, distal faces 150 of the prongs 142 sit flush against the distal faces 134 of the recesses 132. Inner surfaces 146 are adapted for positive engagement with the proximal body portion 128 to facilitate the transmission of torsional loads from the driver 116 to the suture connector 102. The cutouts 152 and the through hole 130 form an enclosed passageway for conducting the suture 106 as the suture 106 traverses the proximal body portion 129 when engaged by the engagement portion 136 of the driver 116. In one embodiment, the driver 116 and suture connector 102 may be reversibly coupled together via any suitable method such as, for example, snap fit, friction fit, etc., for easy and fast insertion of the suture connector 102.

Figure 9:
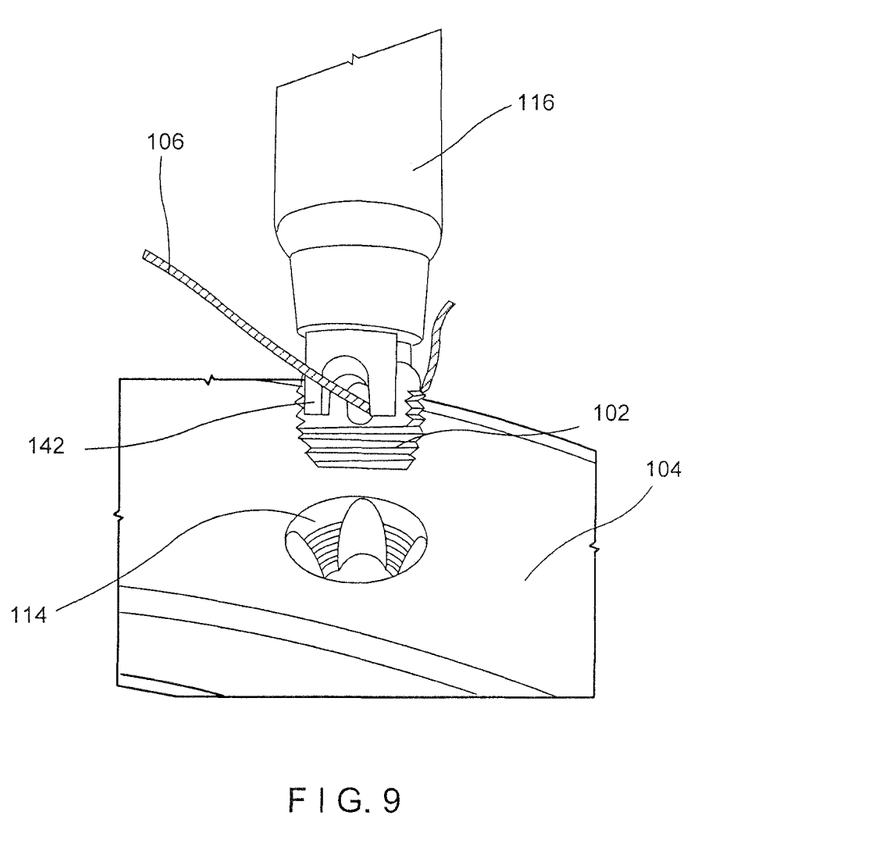
FIG. 9 illustrates a perspective view of the driver engaging the suture connector in a plate hole according to the exemplary embodiment of FIG. 1.

FIG. 9 illustrates an exemplary method for securing a suture 106 to a bone plate 104 using one or more suture connectors 102 and driver 116 according to the current embodiments. In the exemplary method, the bone plate 104 is secured to a portion of bone using any method such as, for example, by applying one or more bone fixation elements (e.g., bone screws) through the plate 104 into the bone. One or more sutures 106 may be attached passed through the through holes 130 of one or more suture connectors 102 before they are inserted into the body. Those skilled in the art will understand that the sutures may be passed through the suture connectors 102 after they have been inserted into the body. However, this is likely to be more difficult. In another embodiment, one or more sutures 106 may be attached to the suture connector 102 after the suture connector 102 has been inserted into the plate 104. The sutures 106 may be attached to the suture connector 102 in any suitable fashion.

In an exemplary embodiment, a suture connector 102 is connected to the distal end of the driver 116, as described above, (e.g., via friction fit) for easy insertion of the suture connector 102 to the bone plate 104. The suture connector 102 and driver 116 are then advanced through the incision to the bone plate 104 which is already fixed to the bone. The proximal end of the driver 116 may include a handle and/or controller (not shown) which, during use, remains outside the body accessible to the user. Once the driver 116 has been advanced to the desired location on the plate 104, the suture connector 102 is inserted into a selected one of the plurality of holes 114 of the bone plate 104. The plurality of positions available for insertion of the suture connector 102 enable the placement of one or more suture connectors 102 and/or sutures 106 according to the needs of the surgeon at the time of placement of the plate 104, the suture connector 102, and the sutures 106.

The suture connector 102 is inserted into the desired hole 114 by rotation of the driver 116, as shown in FIG. 9, to thread the suture connector 102 as the threading 126 of the suture connector 102 engages the plate hole threading. Thus, rotation of the suture connector 102 within the plate hole draws the body 118 of the suture connector 102 into the plate hole to lock the suture connector 102 thereto. Because the cutouts 152 of the prongs 142 are aligned with the through hole 130 of proximal engagement portion 128, the suture 106 remains free and easily maneuverable before, during, and after rotation of the driver 116 and the suture connector 102. As shown in FIG. 9, because of recesses 132, the prongs 142 of the driver 116 easily fit between the proximal engagement portion 128 of the suture connector 102 and the wall of the hole 114.

Once the suture connector 102 has been fully inserted into the hole 114 so that it is flush with the hole 114, the driver 116 is disconnected from the suture connector 102. Those skilled in the art will understand that the suture connector 102 may be oriented in a final position as desired so that an axis of the through hole 130 extends substantially parallel to a direction along which it is desired to have the suture pass therethrough as it is wrapped around the plate 104. If the driver 116 is reversibly coupled (e.g., via a snap fit) to the connector 102, a proximal force may be applied to the driver 116 to uncouple the driver from the suture connector 102. The driver 116 is then removed from the body. In an exemplary embodiment, if the user (i.e. physician) subsequently realizes that the position of the suture 106 is not proper, the suture connector 102 may be removed engaging the driver 116 with a previously mounted suture connector 102 and rotating the suture connector 102 in the opposite direction from insertion. The suture connector 102 may then be repositioned in a different hole 114 using the same method described above.

It will be understood by those of skill in the art that various modifications and variations can be made in the structure and methodology of the present invention without departing from the spirit or scope of the invention. Thus, it is intended that the present invention cover the modifications and variations of this invention provided that they come within the scope of the appended claims and their equivalents.

What is claimed is:

1. A suture connection system, comprising:
    a suture connector, comprising:
        a connector body configured to be inserted into a hole in a bone plate, the connector body having a proximal end, a distal end, a length extending between the proximal end and the distal end substantially corresponding to a thickness of the bone plate, and a sidewall threaded to secure the suture connector to the bone plate;
        the connector body including a first recess extending inwardly from the sidewall to define a first side-face and
        a through hole, configured to receive a suture, the through hole extending through the first side-face and open to the recess; and
    a driver including an elongated rod extending from a proximal end to a distal end along a longitudinal axis of the driver and an engagement element coupled to the distal end of the rod, the engagement element having a first prong configured to engage the first side-face.

2. The system of claim 1, wherein the connector body includes a second recess extending inwardly from the sidewall to define a second side-face and wherein the engagement element includes a second prongs configured to engage the second side-face.

3. The system of claim 2, wherein the first and second prongs are separated from one another by a distance selected so that the first prong may be positioned in the first recess while the second prongs is positioned in the second recess to engage the first and second side.

4. The system of claim 1, wherein the first prong includes a cutout.

5. The system of claim 4, wherein the first cutout extends from a distal face of the first prong to a rounded proximal cutout edge of the first prong, the proximal cutout edge of the first prong aligning with a proximal edge of the through hole so that no portion of the first prong obstructs the through hole.

6. The system of claim 1, wherein the suture connector is sized and shaped to sit flush within the bone plate hole such that no portion of the suture connector extends past an upper surface or a lower surface of the bone plate.

7. A bone plate assembly, comprising:
    a plate having an upper surface, a lower surface and a plurality of holes extending through the plate form the upper surface to the lower surface; and
    at least one suture connector positioned in one of the holes of the plate, the suture connector comprising:
        a body having a proximal end, a distal end, a sidewall, a first recess extending inwardly from the sidewall, and a through hole open to the first recess, the body including a threading to threadedly engage the hole of the plate, and
    a driver extending from a proximal end to a distal end including an engagement element, the engagement element having a first prong configured to engage a first side-face of the first recess.

8. The assembly of claim 7, wherein the body includes a second recess extending inwardly from the sidewall to define a second side-face, and wherein the through hole is open to the second recess and wherein the engagement element includes a second prongs.

9. The assembly of claim 7, wherein the first prong includes a cutout.

10. The assembly of claim 9, wherein the cutout extends from a distal prong face of the first prone to a rounded proximal cutout edge of the first prong, the proximal cutout edge of the first prong aligning with a proximal edge of the through hole so that, when the first prong engages the first side-face, no portion of the first prong obstructs the through hole.

11. The assembly of claim 7, wherein each of the holes is one of a locking hole and a variable angle locking holes.

12. The assembly of claim 7, wherein the suture connector is sized and shaped to sit flush within the bone plate hole such that no portion of the suture connector extends past an upper surface or a lower surface of the bone plate.

13. A method for connecting a suture to a bone, comprising:

securing a bone plate to the bone, the bone plate having a plurality of holes extending through the plate from an upper surface to a lower surface;

inserting a first suture into a suture connector, the first suture connector comprising:
  a body having a proximal end, a distal end, a sidewall, a first recess extending inwardly from the first sidewall, and a through hole open to the first recess, the body including a threading to threadedly engage a first one of the holes of the plate, positioning the first suture connector in the first holes, and using a driver, rotating the first suture connector until the first suture connector is threadedly inserted into the first hole, the driver including an elongated rod and an engagement element coupled to the distal end of the rod, the engagement element including a first prong configured to engage the first side-face.

14. The method of claim 13, wherein rotation of the driver transmits torsional loads from the driver to the first suture connector to rotate the first suture connector.

15. The method of claim 13, further comprising:
removing the first suture connector from the first hole;
repositioning the first suture connector at a second one of the plurality of holes; and
inserting the first suture connector, using the driver, into the second one of the plurality of holes.

16. The method of claim 13, wherein the body includes a second recess extending inwardly from the sidewall, and wherein the through hole is open to the second recess, wherein the engagement element includes a second prongs, the second prongs being configured to engage the second side-face.

17. The method of claim 13, wherein the first prong includes a cutout, the cutout extending from a distal prong face of the first prong to a rounded proximal cutout edge of the first prong, the proximal cutout edge of the first prong aligning with a proximal edge of the through hole so that no portion of the first prong obstructs the through hole.

* * * * *